United States Patent
Akahane et al.

(10) Patent No.: US 9,693,002 B2
(45) Date of Patent: Jun. 27, 2017

(54) IMAGE SENSOR, IMAGING DEVICE, ENDOSCOPE, AND ENDOSCOPE SYSTEM

(71) Applicant: OLYMPUS CORPORATION, Tokyo (JP)

(72) Inventors: Nana Akahane, Yamanashi (JP); Susumu Yamazaki, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/331,964

(22) Filed: Oct. 24, 2016

(65) Prior Publication Data

US 2017/0041561 A1 Feb. 9, 2017

Related U.S. Application Data

(63) Continuation of application No. PCT/JP2015/079217, filed on Oct. 15, 2015.

(30) Foreign Application Priority Data

Nov. 25, 2014 (JP) .................................. 2014-238042

(51) Int. Cl.
*H04N 5/357* (2011.01)
*H04N 5/374* (2011.01)
(Continued)

(52) U.S. Cl.
CPC ....... *H04N 5/3698* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 5,153,731 A * 10/1992 Nagasaki ............... H04N 3/155
257/231
5,572,280 A * 11/1996 Yaji ..................... H04N 5/2353
348/229.1
(Continued)

FOREIGN PATENT DOCUMENTS

JP   2008-277915 A   11/2008
JP      5596888 B1    9/2014

OTHER PUBLICATIONS

International Search Report dated Jan. 12, 2016 issued in PCT/JP2015/079217.

*Primary Examiner* — Reza Aghevli
(74) *Attorney, Agent, or Firm* — Scully, Scott, Murphy & Presser, PC

(57) ABSTRACT

An image sensor includes: a plurality of pixels arranged in a two-dimensional matrix form and configured to receive light from outside and generate and output an imaging signal depending on an amount of the received light; a transfer unit configured to transfer the imaging signal output from each of the pixels; a sample-and-hold unit configured to hold and output the imaging signal transferred from the transfer unit; a reference voltage generation unit configured to generate and output a reference voltage; an amplifier connected to the sample-and-hold unit and to the reference voltage generation unit and configured to amplify and output the imaging signal input from the sample-and-hold unit using the reference voltage as a reference; and a control unit configured to control the reference voltage to be input to the amplifier during at least one of a horizontal blanking period and a video signal period of the imaging signal.

8 Claims, 11 Drawing Sheets

(51) Int. Cl.
    *H04N 5/378*     (2011.01)
    *A61B 1/00*     (2006.01)
    *H04N 5/369*     (2011.01)
    *A61B 1/04*     (2006.01)
    *A61B 1/045*     (2006.01)
    *A61B 1/05*     (2006.01)
    *H04N 5/225*     (2006.01)

(52) U.S. Cl.
    CPC ................ *A61B 1/04* (2013.01); *A61B 1/045* (2013.01); *A61B 1/051* (2013.01); *H04N 5/2256* (2013.01); *H04N 5/357* (2013.01); *H04N 5/374* (2013.01); *H04N 5/378* (2013.01); *H04N 2005/2255* (2013.01)

(56) References Cited

U.S. PATENT DOCUMENTS

| | | | | |
|---|---|---|---|---|
| 6,452,632 B1* | 9/2002 | Umeda | ................... | H04N 3/155 348/294 |
| 2009/0256060 A1* | 10/2009 | Meynants | ............... | H04N 5/353 250/208.1 |
| 2009/0322912 A1* | 12/2009 | Blanquart | ............ | H04N 5/2351 348/241 |
| 2014/0320618 A1 | 10/2014 | Akahane et al. | | |
| 2015/0237275 A1* | 8/2015 | Iwata | ................... | H04N 5/3598 348/241 |

* cited by examiner

US 9,693,002 B2

IMAGE SENSOR, IMAGING DEVICE, ENDOSCOPE, AND ENDOSCOPE SYSTEM

CROSS REFERENCES TO RELATED APPLICATIONS

This application is a continuation of PCT international application Ser. No. PCT/JP2015/079217, filed on Oct. 15, 2015 which designates the United States, incorporated herein by reference, and which claims the benefit of priority from Japanese Patent Application No. 2014-238042, filed on Nov. 25, 2014, incorporated herein by reference.

BACKGROUND

1. Technical Field

The disclosure relates to an image sensor for imaging an object to generate image data of the object. The disclosure also relates to an imaging device, an endoscope, and an endoscope system.

2. Related Art

Conventionally, an image sensor such as a complementary metal-oxide semiconductor (CMOS) image sensor is configured such that imaging signals transferred row by row are held in a sample-and-hold circuit and sequentially output to a horizontal output signal line for each pixel by a column reading circuit, whereby the imaging signals are read, and the signals are output from an output amplifier circuit. In addition, in order to prevent a deterioration in a response property when a large amount of light enters a photoelectric conversion device, such a technique is conventionally known that a clip voltage of an amplifier circuit is set by an output voltage of a reference voltage circuit (for example, refer to JP 2008-277915 A). Specifically, the reference voltage circuit includes an operational amplifier in which a current source, a plurality of resistors, and a plurality of transistors are used. Generally, the reference voltage circuit disclosed in JP 2008-277915 A is used for a reference voltage of an output amplifier circuit in an image sensor, whereby a video signal is output with a high degree of accuracy.

SUMMARY

In some embodiments, an image sensor includes: a plurality of pixels arranged in a two-dimensional matrix form and configured to receive light from outside and generate and output an imaging signal depending on an amount of the received light; a transfer unit configured to transfer the imaging signal output from each of the plurality of pixels; a sample-and-hold unit configured to hold and output the imaging signal transferred from the transfer unit; a reference voltage generation unit configured to generate and output a reference voltage; an amplifier connected to the sample-and-hold unit and to the reference voltage generation unit and configured to amplify and output the imaging signal input from the sample-and-hold unit using the reference voltage as a reference; and a control unit configured to control the reference voltage to be input to the amplifier during at least one of a horizontal blanking period and a video signal period of the imaging signal.

In some embodiments, an imaging device includes the image sensor.

In some embodiments, an endoscope includes an insertion portion that has the imaging device on a distal end of the insertion portion.

In some embodiments, an endoscope system includes the endoscope, and a processing device configured to convert the imaging signal into an image signal.

The above and other features, advantages and technical and industrial significance of this invention will be better understood by reading the following detailed description of presently preferred embodiments of the invention, when considered in connection with the accompanying drawings.

DETAILED DESCRIPTION

As modes for carrying out the present invention (hereinafter referred to as "embodiment(s)"), reference will be made to an exemplary endoscope system having an imaging device. The present invention is not limited by the embodiments. The same reference signs are used to designate the same elements throughout the drawings. Note that the drawings are only schematic, and a relation between thickness and width of each member and a ratio of each member or the like are different from actual ones. Dimensions and ratios in the different drawings may also be different from one another.

First Embodiment

Configuration of Endoscope System

Figure 1:
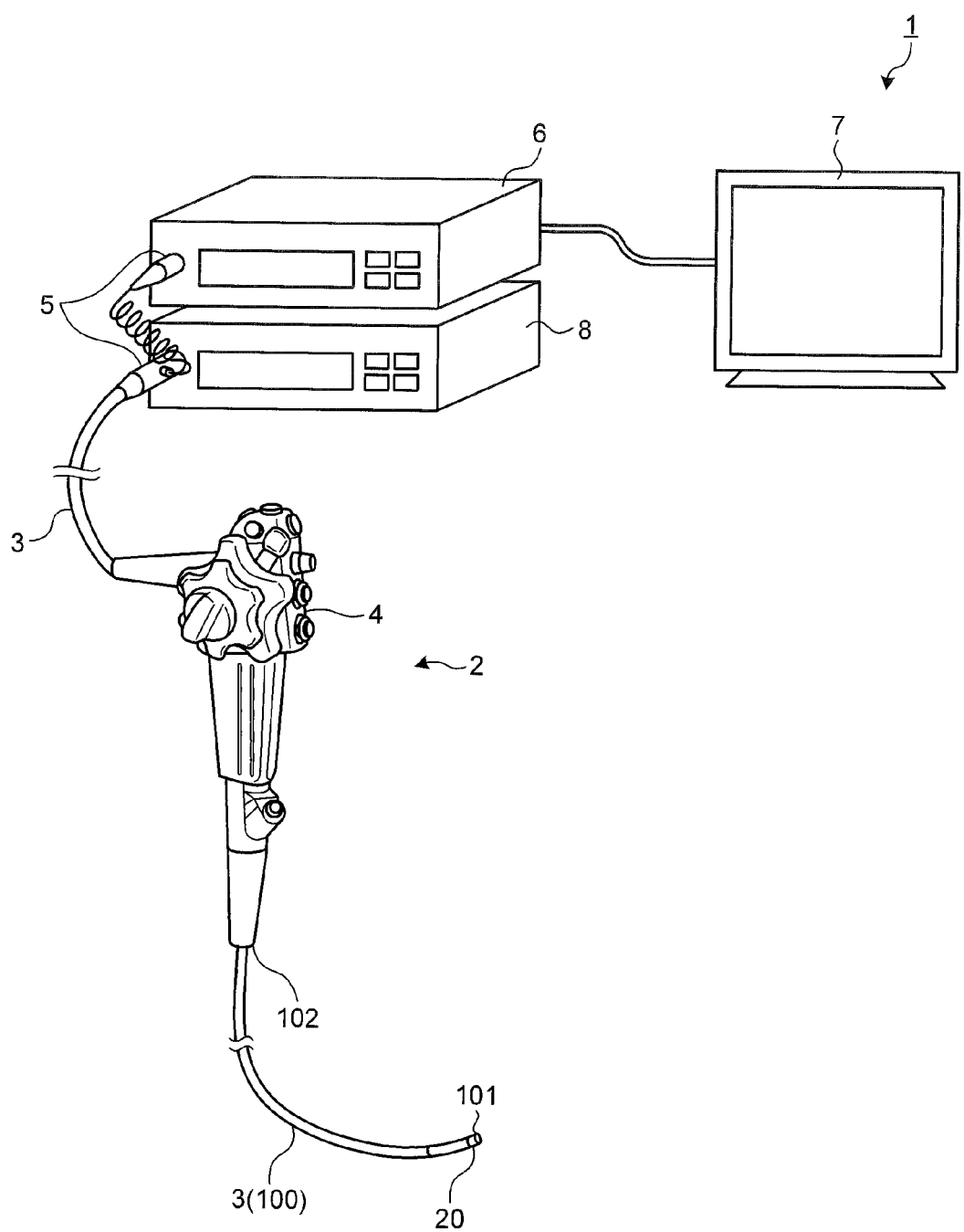
FIG. 1 is a schematic view illustrating an overall configuration of an endoscope system according to a first embodiment of the present invention.

FIG. 1 is a schematic view illustrating an overall configuration of an endoscope system according to a first embodiment of the present invention. An endoscope system 1 illustrated in FIG. 1 includes an endoscope 2, a transmission cable 3, a connector unit 5, a processor 6 (processing device), a display device 7, and a light source device 8.

An insertion portion 100 that is a part of the transmission cable 3 is inserted into a body cavity of a subject, whereby the endoscope 2 captures an in-vivo image of the subject and outputs an imaging signal (image data) to the processor 6. The endoscope 2 is configured such that an imaging unit 20 (imaging device) that captures the in-vivo image is provided on one end side of the transmission cable 3 and on a side close to a distal end 101 of the insertion portion 100 that is inserted into the body cavity of the subject. An operating unit 4 that accepts various types of operation for the endoscope 2 is connected on a side close to a proximal end 102 of the insertion portion 100. The imaging unit 20 is coupled to the connector unit 5 by the transmission cable 3 via the operating unit 4. The imaging signal of the image captured by the imaging unit 20 passes through the transmission cable 3 having a length of, for example, a few meters, and is output to the connector unit 5.

The connector unit 5 is connected to the endoscope 2, the processor 6, and the light source device 8. The connector unit 5 performs a predetermined signal process for the imaging signal output by the connected endoscope 2, and converts the imaging signal from an analog signal into a digital signal (A/D conversion) to output it to the processor 6 as an image signal.

The processor 6 performs a predetermined image process on the image signal output from the connector unit 5, and controls the entire endoscope system 1. In the first embodiment, the processor 6 functions as a processing device.

The display device 7 displays the image corresponding to the image signal subjected to the image process by the processor 6. The display device 7 also displays various types of information about the endoscope system 1.

The light source device 8 includes, for example, a halogen lamp and a white light emitting diode (LED) or the like. The light source device 8 emits illumination light from a distal end side of the insertion portion 100 of the endoscope 2 through the connector unit 5 and the transmission cable 3 toward an object.

Figure 2:
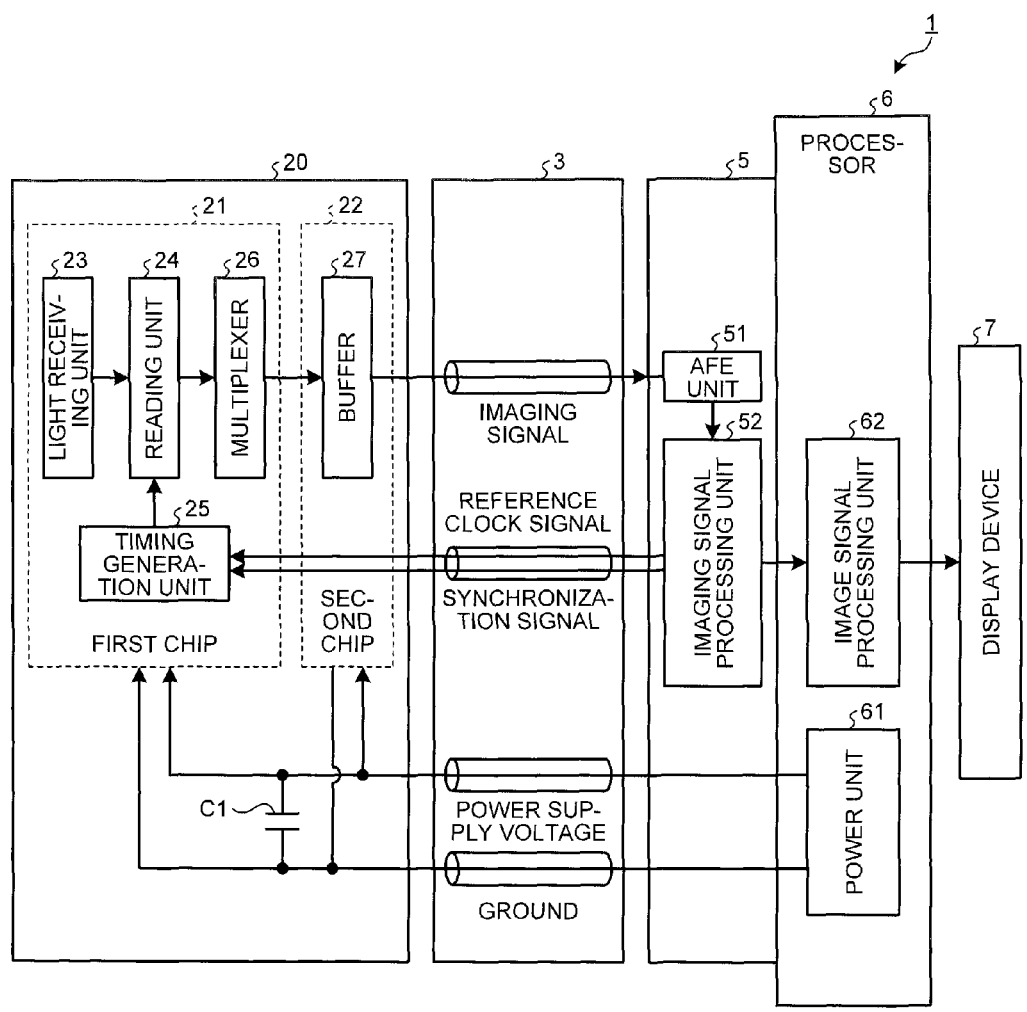
FIG. 2 is a block diagram illustrating a function of a principal part of the endoscope system according to the first embodiment of the present invention.

FIG. 2 is a block diagram illustrating a function of a principal part of the endoscope system 1. With reference to FIG. 2, a detailed configuration of each element of the endoscope system 1 and a path for an electric signal within the endoscope system 1 will be described.

As illustrated in FIG. 2, the imaging unit 20 includes a first chip 21 (image sensor) and a second chip 22.

The first chip 21 has a light receiving unit 23, a reading unit 24, a timing generation unit 25, and a multiplexer 26. The light receiving unit 23 is configured such that a plurality of unit pixels is arranged in a two-dimensional matrix form. The reading unit 24 reads the imaging signal subjected to a photoelectric conversion in the light receiving unit 23. The timing generation unit 25 generates a timing signal based on a reference clock signal and a synchronization signal input from the connector unit 5 and outputs the timing signal to the reading unit 24. The multiplexer 26 temporarily holds the imaging signal read from the light receiving unit 23 by the reading unit 24 and a reference signal, and alternately outputs the imaging signal and the reference signal. A more detailed configuration of the first chip 21 will be described later with reference to FIG. 3.

The second chip 22 has a buffer 27 that functions as a sending unit configured to send the imaging signal output from the first chip 21 to the processor 6 through the transmission cable 3 and the connector unit 5. A combination of circuits mounted on the first chip 21 and the second chip 22 can be appropriately changed in accordance with the convenience of setting.

The imaging unit 20 receives, through the transmission cable 3, a power supply voltage VDD together with a ground GND. The power supply voltage VDD is generated in a power unit 61 within the processor 6. A capacitor C1 for power supply stabilization is provided between the power supply voltage VDD and the ground GND supplied to the imaging unit 20.

The connector unit 5 has an analog front end unit 51 (hereinafter referred to as the "AFE unit 51") and an imaging signal processing unit 52. The connector unit 5 electrically connects the endoscope 2 (imaging unit 20) to the processor 6 and functions as a relay processor that relays an electric signal. The connector unit 5 and the imaging unit 20 are coupled by the transmission cable 3. The connector unit 5 and the processor 6 are coupled by, for example, a coil cable. The connector unit 5 is also connected to the light source device 8.

The AFE unit 51 receives the imaging signal transmitted from the imaging unit 20 and performs impedance matching by means of a passive element such as a resistor. After that, the AFE unit 51 extracts an AC component by means of a capacitor and determines an operating point by means of a voltage dividing resistor. Subsequently, the AFE unit 51 performs an analog-digital (A/D) conversion on the analog imaging signal to produce an digital imaging signal, and outputs the digital imaging signal to the imaging signal processing unit 52.

The imaging signal processing unit 52 includes, for example, a field programmable gate array (FPGA). The imaging signal processing unit 52 generates the reference clock signal (for example, a clock of 27 MHz) serving as a reference for operation of each element of the endoscope 2 and the synchronization signal representing a start position of each frame, and supplies the reference clock signal and the synchronization signal to the timing generation unit 25. The imaging signal processing unit 52 also performs a predetermined signal process, such as a noise removal, on the digital imaging signal input from the AFE unit 51.

The processor 6 is a control device that comprehensively controls the entire endoscope system 1. The processor 6 includes the power unit 61 and an image signal processing unit 62.

The power unit 61 generates the power supply voltage VDD and supplies the generated power supply voltage VDD together with the ground GND to the imaging unit 20 through the connector unit 5 and the transmission cable 3.

The image signal processing unit 62 performs an image process on the digital imaging signal subjected to the signal process by the imaging signal processing unit 52 and converts the digital imaging signal into an image signal. The image process includes, for example, a synchronization process, a white balance (WB) adjustment process, a gain adjustment process, a gamma correction process, a digital-analog (D/A) conversion process, and a format conversion process. The image signal processing unit 62 then outputs the image signal to the display device 7.

The display device 7 displays an image captured by the imaging unit 20 based on the image signal input from the image signal processing unit 62. The display device 7 includes, for example, a display panel such as a liquid crystal display panel and an organic electro luminescence (EL) display panel.

Configuration of First Chip

Next, the detailed configuration of the above-mentioned first chip 21 will be described.

Figure 3:
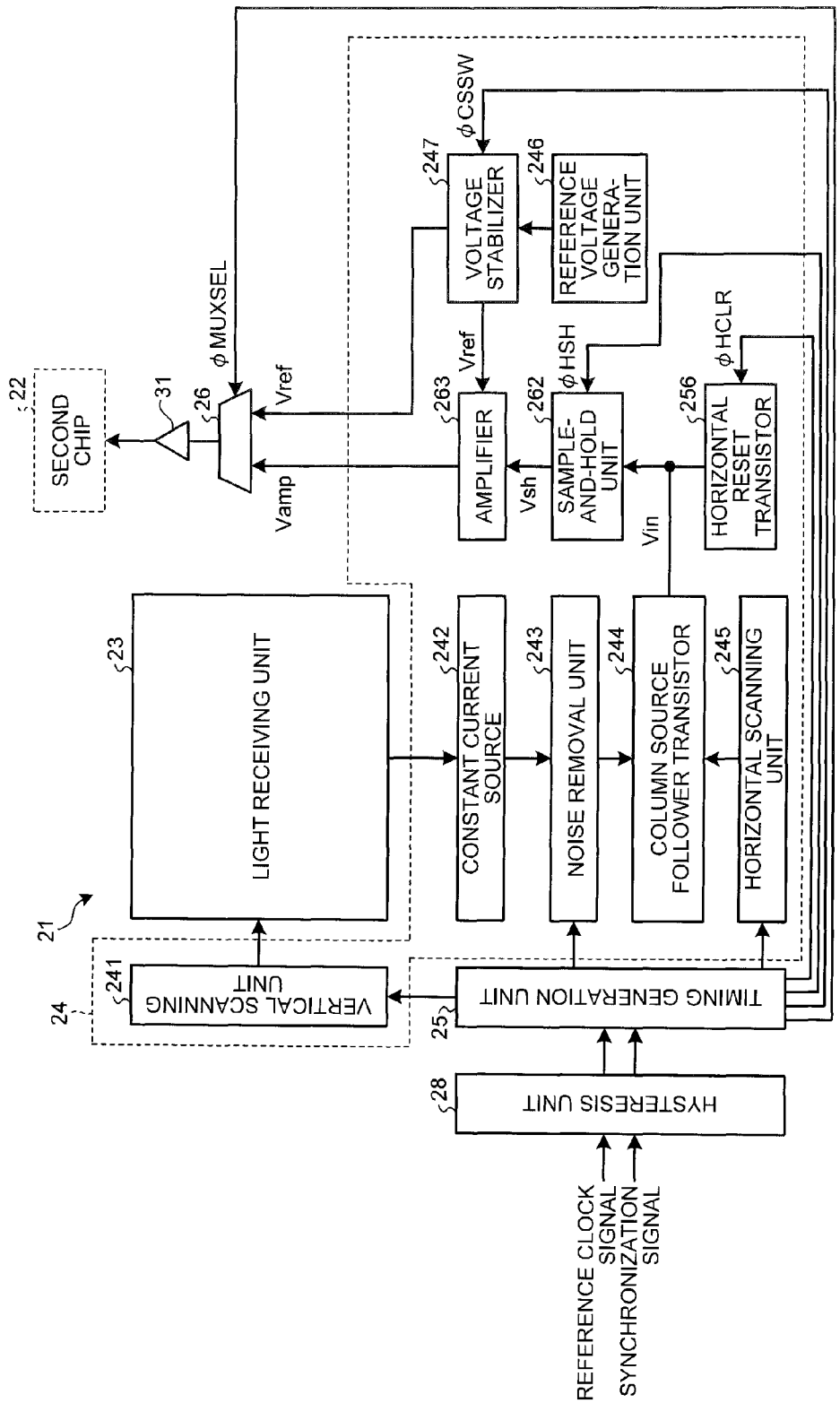
FIG. 3 is a block diagram illustrating a detailed configuration of a first chip illustrated in FIG. 2.
Figure 4:
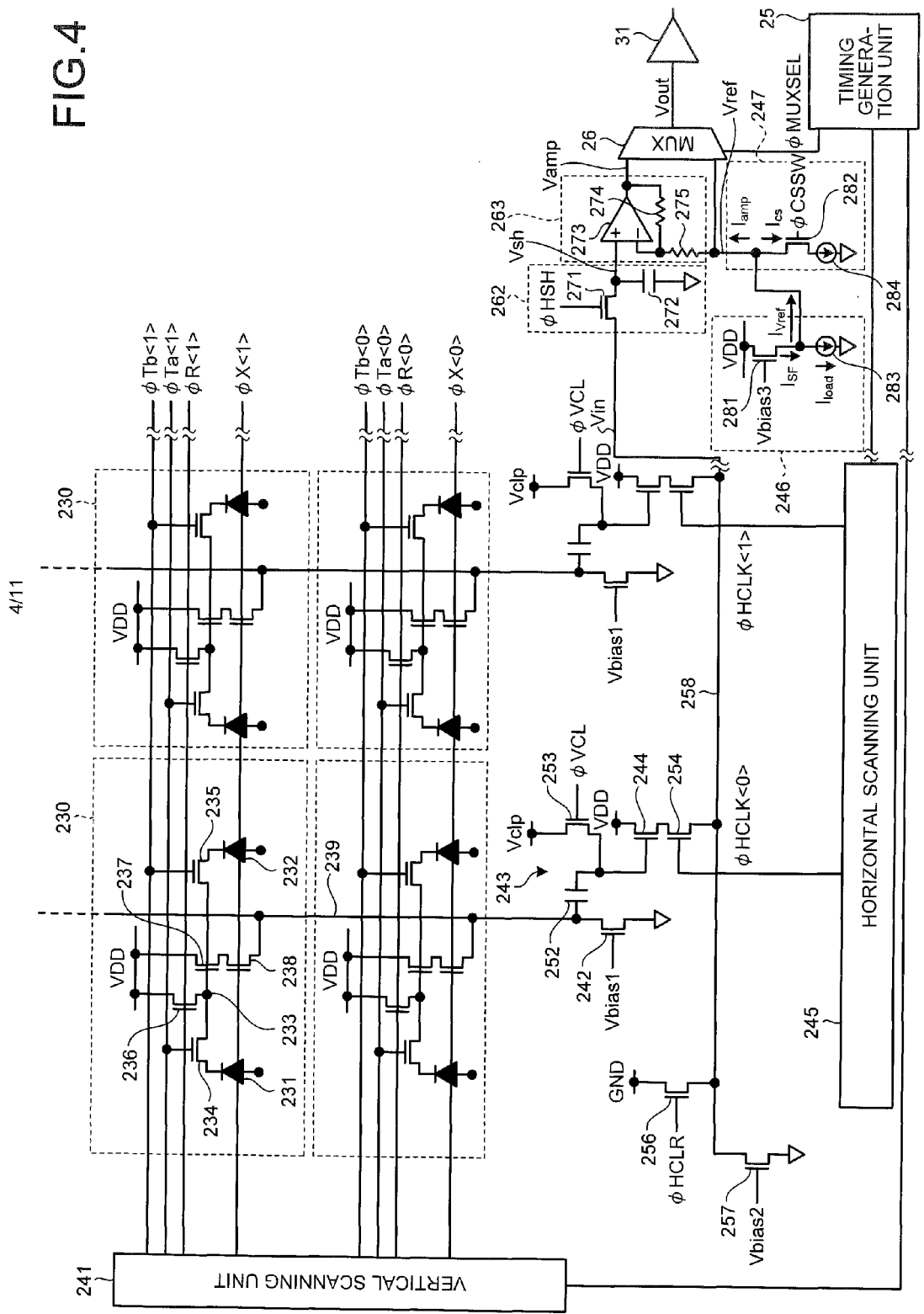
FIG. 4 is a circuit diagram illustrating the detailed configuration of the first chip according to the first embodiment of the present invention.

FIG. 3 is a block diagram illustrating the detailed configuration of the first chip 21 illustrated in FIG. 2. FIG. 4 is a circuit diagram illustrating the configuration of the first chip 21.

As illustrated in FIGS. 3 and 4, the first chip 21 has the light receiving unit 23, the reading unit 24 (drive unit), the timing generation unit 25, the multiplexer 26, a hysteresis unit 28, and an output unit 31 (amplifier).

The hysteresis unit 28 shapes waveforms of the reference clock signal and the synchronization signal input through the transmission cable 3 and outputs, to the timing generation unit 25, the reference clock signal and the synchronization signal subjected to the waveform shaping.

The timing generation unit 25 generates various drive signals (φTa, φTb, φR, φX, φVCL, φHCLR, φHCLK, φMUXSEL, φHSH, φCSSW) based on the reference clock signal and the synchronization signal input from the hysteresis unit 28. The timing generation unit 25 then outputs the respective drive signals to a vertical scanning unit 241 (row selection circuit) of the reading unit 24 which will be described later, a noise removal unit 243, a horizontal scanning unit 245, a horizontal reset transistor 256, a sample-and-hold unit 262, a voltage stabilizer 247 (current source), and the multiplexer 26. In the first embodiment, the timing generation unit 25 functions as a control unit that controls a voltage of a reference voltage Vref input to an amplifier 263 during at least one of a horizontal blanking period and a video signal period of the imaging signal.

The reading unit 24 transfers, to the multiplexer 26, each of the imaging signal and the reference signal. The imaging signal is output from each of a plurality of pixels of the light receiving unit 23 which will be described later. The reference signal is output from a reference voltage generation unit 246.

Hereinafter, a detailed configuration of the reading unit 24 will be described. The reading unit 24 includes the vertical scanning unit 241 (row selection circuit), a constant current source 242, the noise removal unit 243 (noise removal circuit), a column source follower transistor 244, the horizontal scanning unit 245, the reference voltage generation unit 246, and the voltage stabilizer 247.

The vertical scanning unit 241 applies row selection pulses φT<M> and φR<M> to a selected row <M> (M=0, 1, 2 m-1, m) of the light receiving unit 23 based on drive signals (φT, φR or the like) input from the timing generation unit 25. The vertical scanning unit 241 then drives each unit pixel 230 of the light receiving unit 23 by means of the constant current source 242, thereby transferring the imaging signal and a noise signal at the time of a pixel reset to a vertical transfer line 239 (first transfer line), and outputting them to the noise removal unit 243.

The noise removal unit 243 removes an output variation of each unit pixel 230 and the noise signal at the time of the pixel reset, and outputs the imaging signal subjected to the photoelectric conversion in each unit pixel 230. The noise removal unit 243 will be described in detail later.

The horizontal scanning unit 245 applies a column selection pulse φHCLK<N> to a selected column <N> (N=0, 1, 2..., n-1, n) of the light receiving unit 23 based on the drive signal (φHCLK) supplied from the timing generation unit 25. The horizontal scanning unit 245 then transfers the imaging signal subjected to the photoelectric conversion in each unit pixel 230 to a horizontal transfer line 258 (second transfer line) through the noise removal unit 243 and outputs it to the multiplexer 26. In the first embodiment, the horizontal transfer line 258 functions as a transfer unit that transfers the imaging signal output from each unit pixel 230.

On the light receiving unit 23 of the first chip 21, many unit pixels 230 are arranged in the two-dimensional matrix form. Each unit pixel 230 includes a photoelectric conversion element 231 (photodiode), a photoelectric conversion element 232, a charge converter 233, a transfer transistor 234 (first transfer unit), a transfer transistor 235, a charge converter reset unit 236 (transistor), a pixel source follower transistor 237, and a pixel output switch 238 (signal output unit). In the specification, one or more photoelectric conversion elements and transfer transistors for transferring signal charges from the respective photoelectric conversion elements to the charge converter 233 are referred to as a unit cell. In other words, one or more sets of the photoelectric conversion element and the transfer transistor are included in the unit cell, and a single unit cell is included in each unit pixel 230.

Each of the photoelectric conversion element 231 and the photoelectric conversion element 232 photoelectrically converts incident light into a signal charge amount that depends on its amount of light and accumulates the signal charge amount. The photoelectric conversion element 231 and the photoelectric conversion element 232 are respectively connected to one end sides of the transfer transistor 234 and the transfer transistor 235 on cathode sides, and connected to the ground GND on anode sides. The charge converter 233 includes a floating diffusion capacitance (FD) and converts the charges accumulated in the photoelectric conversion element 231 and the photoelectric conversion element 232 into voltages.

The transfer transistor 234 and the transfer transistor 235 transfer the charges respectively from the photoelectric conversion element 231 and the photoelectric conversion element 232 to the charge converter 233. Signal lines are connected to respective gates of the transfer transistor 234 and the transfer transistor 235. Drive pulses (row selection pulses) φTa and φTb are supplied to the respective signal lines. The transfer transistor 234 and the transfer transistor 235 are connected to the charge converter 233 on the other end sides. The transfer transistor 234 and the transfer transistor 235 are turned on when the drive pulses φTa and φTb are supplied from the vertical scanning unit 241 through the signal lines. The transfer transistor 234 and the transfer transistor 235 then transfer the signal charges from the photoelectric conversion element 231 and the photoelectric conversion element 232 to the charge converter 233.

The charge converter reset unit 236 resets the charge converter 233 to a predetermined potential. The charge converter reset unit 236 is connected to the power supply voltage VDD on one end side and connected to the charge converter 233 on the other end side. A signal line is connected to a gate of the charge converter reset unit 236, and a drive pulse φR is supplied to the signal line. The charge converter reset unit 236 is turned on when the drive pulse φR is supplied from the vertical scanning unit 241 through the signal line. The charge converter reset unit 236 then discharges the signal charges accumulated in the charge converter 233, whereby the charge converter 233 is reset to the predetermined potential.

The pixel source follower transistor 237 is connected to the power supply voltage VDD on one end side and connected to one end side of the pixel output switch 238 on the other end side. The signal (imaging signal or signal at the time of the reset) subjected to the voltage conversion in the charge converter 233 is input to a gate of the pixel source follower transistor 237.

The pixel output switch 238 outputs, to the vertical transfer line 239, the signal subjected to the voltage conversion in the charge converter 233. The pixel output switch 238 is connected to the vertical transfer line 239 on the other end side. A signal line is connected to a gate of the pixel output switch 238, and a drive pulse φX is supplied to the signal line. The pixel output switch 238 is turned on when the drive pulse φX is supplied from the vertical scanning unit 241 to the gate of the pixel output switch 238 through the signal line. The pixel output switch 238 then transfers the imaging signal or the signal at the time of the reset to the vertical transfer line 239.

The constant current source 242 is connected to the vertical transfer line 239 on one end side and connected to the ground GND on the other end side. A bias voltage Vbias1 is applied to a gate of the constant current source 242. The constant current source 242 drives the unit pixel 230 by means of the constant current source 242 and reads the output of the unit pixel 230 to the vertical transfer line 239. The signal read to the vertical transfer line 239 is input to the noise removal unit 243.

The noise removal unit 243 includes a transfer capacitance 252 (AC coupling capacitor) and a clamp switch 253 (transistor).

The transfer capacitance 252 is connected to the vertical transfer line 239 on one end side and connected to the column source follower transistor 244 on the other end side.

The clamp switch 253 is connected to a signal line on one end side. A clamp voltage Vclp is supplied from the reference voltage generation unit 246 to the signal line. The clamp switch 253 is connected between the transfer capacitance 252 and the column source follower transistor 244 on the other end side. The drive signal φVCL is input from the timing generation unit 25 to a gate of the clamp switch 253. The imaging signal input to the noise removal unit 243 is an optical noise sum signal including a noise component.

The clamp switch 253 is turned on when the drive signal φVCL is input from the timing generation unit 25 to the gate of the clamp switch 253. The transfer capacitance 252 is then reset by the clamp voltage Vclp supplied from the reference voltage generation unit 246. The imaging signal subjected to a noise removal in the noise removal unit 243 is input to a gate of the column source follower transistor 244.

Since the noise removal unit 243 does not require a sampling capacitor (sampling capacitance), the capacitance of the transfer capacitance 252 (AC coupling capacitor) only needs to be a capacitance that is sufficient for an input capacitance of the column source follower transistor 244. In addition, owing to the absence of the sampling capacitance of the noise removal unit 243, an area occupied by the noise removal unit 243 in the first chip 21 can be reduced.

The column source follower transistor 244 is connected to the power supply voltage VDD on one end side and connected to one end side of a column selection switch 254 (second transfer unit) on the other end side. The imaging signal subjected to the noise removal in the noise removal unit 243 is input to the gate of the column source follower transistor 244.

The column selection switch 254 is connected, on one end side, to the other end side of the column source follower transistor 244 and connected to the horizontal transfer line 258 (second transfer line) on the other end side. A signal line is connected to a gate of the column selection switch 254 and configured to supply a drive signal φHCLK<M> from the horizontal scanning unit 245. The column selection switch 254 is turned on when the drive signal φHCLK<M> is supplied from the horizontal scanning unit 245 to the gate of the column selection switch 254 of a column <M>. The column selection switch 254 then transfers the signal of the vertical transfer line 239 of the column <M> (imaging signal subjected to the noise removal in the noise removal unit 243) to the horizontal transfer line 258.

The horizontal reset transistor 256 is connected to the ground GND on one end side and connected to the horizontal transfer line 258 on the other end side. The drive signal φHCLR is input from the timing generation unit 25 to a gate of the horizontal reset transistor 256. The horizontal reset transistor 256 is turned on when the drive signal φHCLR is input from the timing generation unit 25 to the gate of the horizontal reset transistor 256. The horizontal reset transistor 256 then resets the horizontal transfer line 258.

A constant current source 257 is connected to the horizontal transfer line 258 on one end side and connected to the ground GND on the other end side. A bias voltage Vbias2 is applied to a gate of the constant current source 257. The constant current source 257 reads the imaging signal from the vertical transfer line 239 to the horizontal transfer line 258. The signal read to the horizontal transfer line 258 is input to the sample-and-hold unit 262.

The sample-and-hold unit 262 holds and outputs the imaging signal transferred from the horizontal transfer line 258. The sample-and-hold unit 262 has a sample-and-hold switch 271 (transistor) and a sample capacitance 272 (capacitor).

The sample-and-hold switch 271 is connected to the horizontal transfer line 258 on one end side and connected, on the other end side, to input of an operational amplifier 273 of the amplifier 263 which will be described later. A signal line is connected to a gate of the sample-and-hold switch 271 and configured to supply the drive signal φHSH.

The sample capacitance 272 is provided between the sample-and-hold switch 271 and the amplifier 263. The sample capacitance 272 is connected, on one end side, to the other end side of the sample-and-hold switch 271 and the input of the operational amplifier 273 of the amplifier 263, and connected to the ground GND on the other end side.

The sample-and-hold unit 262 configured in this manner is turned on when the drive signal φHSH is input from the timing generation unit 25 to the gate of the sample-and-hold switch 271. The sample-and-hold unit 262 then causes the sample capacitance 272 to hold a voltage input to the sample capacitance 272 through the horizontal transfer line 258 immediately before the sample-and-hold unit 262 is turned off. The sample-and-hold unit 262 is turned off when the drive signal φHSH input from the timing generation unit 25 to the gate of the sample-and-hold switch 271 stops. The sample-and-hold unit 262 then outputs the voltage (signal) held in the sample capacitance 272 to the operational amplifier 273 of the amplifier 263 which will be described later.

The amplifier 263 amplifies the signal input from the sample-and-hold unit 262 using the reference voltage Vref input from the reference voltage generation unit 246 which will be described later as a reference. The amplifier 263 then outputs the signal to the multiplexer 26. The amplifier 263 has the operational amplifier 273, a first resistor 274, and a second resistor 275. The operational amplifier 273 is connected to the other end side of the sample-and-hold switch 271 on an input side (positive side terminal) and connected to the multiplexer 26 on an output side. Output of the operational amplifier 273 is input to an inverting input terminal (negative side terminal) of the operational amplifier 273 through the first resistor 274. The reference voltage Vref is input from the reference voltage generation unit 246 to the inverting input terminal (negative side terminal) of the operational amplifier 273 through the second resistor 275 and the voltage stabilizer 247.

In the first embodiment, the read of the imaging signal after the noise removal from the vertical transfer line 239 and the reset of the horizontal transfer line 258 by the horizontal reset transistor 256 are alternately performed, whereby crosstalk of the imaging signal in a column direction can be suppressed. The sample-and-hold switch 271 of the sample-and-hold unit 262 is turned on when the imaging signal after the noise removal is transferred, and turned off at the time of the reset, whereby only the imaging signal after the noise removal can be output to the amplifier 263. Since the first chip 21 includes the sample-and-hold unit 262, a bandwidth of an amplifier circuit at a later stage can be reduced by half, and a range can be suppressed.

The reference voltage generation unit 246 generates and outputs the reference voltage Vref. The reference voltage generation unit 246 has a source follower transistor 281. The source follower transistor 281 is connected to the power supply voltage VDD on one end side and connected to one end side of a constant current source 283 on the other end side. A signal line is connected to a gate of the source follower transistor 281, and a bias voltage Vbias3 is supplied to the signal line. The reference voltage generation unit 246 outputs the reference voltage Vref to the voltage stabilizer 247.

Hereinafter, the reference voltage Vref (output voltage) that is output by the reference voltage generation unit 246 will be described. In the first embodiment, the reference voltage Vref is obtained using the following Formulas (1) and (2).

$$V_{ref} = V_{bias} - V_T - \sqrt{\frac{2I_{SF}}{\beta}} \quad (1)$$

$$\beta = \frac{1}{2}\mu Cox\left(\frac{W}{L}\right) \quad (2)$$

In the formulas, $V_T$ is a threshold voltage of the source follower transistor 281, $\mu$ is mobility of the source follower transistor 281, Cox is a gate capacitance per unit area of the source follower transistor 281, W is a gate width of the source follower transistor 281, and L is a gate length of the source follower transistor 281.

The voltage stabilizer 247 is provided between the reference voltage generation unit 246 and the amplifier 263 and keeps the reference voltage Vref generated by the reference voltage generation unit 246 constant (stabilization). The voltage stabilizer 247 has a switch 282 (transistor). The switch 282 is connected, on one end side, to a line connecting the reference voltage generation unit 246 to the operational amplifier 273 of the amplifier 263, and connected to one end side of a constant current source 284 on the other end side. A signal line is connected to a gate of the switch 282, and the drive signal φCSSW is supplied from the timing generation unit 25 to the signal line. The voltage stabilizer 247 is turned on when the drive signal φCSSW is input from the timing generation unit 25 to the gate of the switch 282 during the horizontal blanking period of the imaging signal, whereby current $I_{cs}$ flows. Consequently, the reference voltage Vref input to the operational amplifier 273 of the amplifier 263 is kept constant whether the horizontal blanking period or the video signal period.

The multiplexer 26 alternately outputs, to the output unit 31, the imaging signal subjected to the noise removal and output from the sample-and-hold unit 262 and the reference voltage Vref generated in the reference voltage generation unit 246.

The output unit 31 subjects the imaging signal subjected to the noise removal and the reference voltage Vref to signal amplification as necessary. The output unit 31 then alternately outputs the imaging signal and the reference voltage Vref to the second chip 22.

The second chip 22 transmits, to the connector unit 5 through the transmission cable 3, only an AC component of the imaging signal subjected to the noise removal and the reference voltage Vref.

Operation of First Chip

Figure 5:
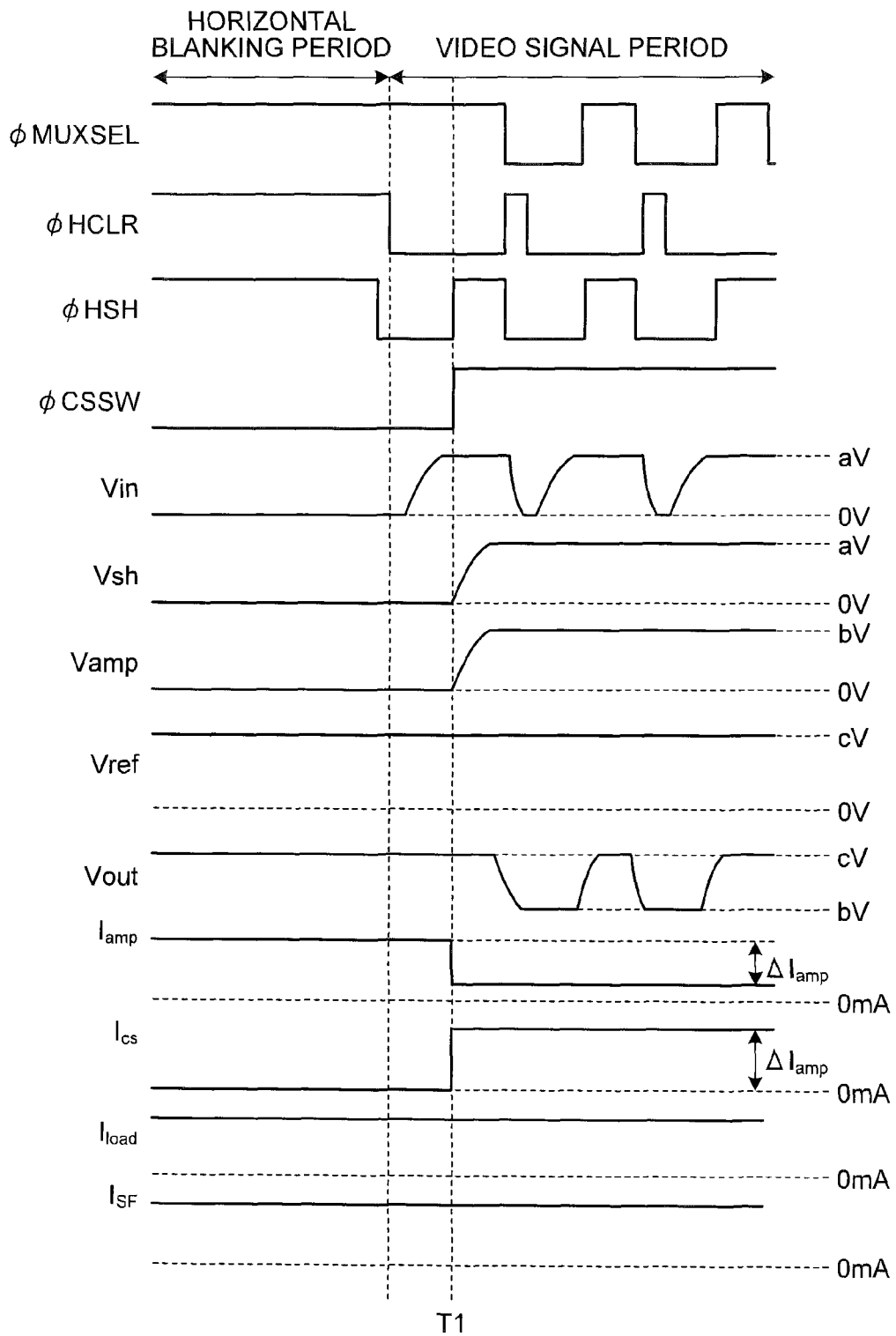
FIG. 5 is a timing chart illustrating a drive timing of the first chip according to the first embodiment of the present invention.

Next, the operation of the first chip 21 will be described. FIG. 5 is a timing chart illustrating a drive timing of the first chip 21. In FIG. 5, in order from the highest stage, the drive signals φMUXSEL, φHCLR, φHSH, φCSSW, an input voltage Vin, a voltage Vsh, a voltage Vamp, the reference voltage Vref, an output voltage Vout, current $I_{amp}$, the current $I_{cs}$, current $I_{load}$, and current $I_{SF}$ are illustrated. In FIG. 5, the drive timing from input of the imaging signal as the input voltage Vin from the light receiving unit 23 until output of the imaging signal will be described.

First, as illustrated in FIG. 5, during the horizontal blanking period of the imaging unit 20, the timing generation unit 25 turns the multiplexer 26 on (φMUXSEL: High), turns the horizontal reset transistor 256 on (φHCLR: High), and turns the sample-and-hold switch 271 of the sample-and-hold unit 262 on (φHSH: High). Consequently, during the horizontal blanking period of the imaging signal, the reference voltage Vref is output from the multiplexer 26 to the output unit 31 as the output voltage Vout (for example, cV).

Next, the timing generation unit 25 turns the sample-and-hold switch 271 of the sample-and-hold unit 262 off (φHSH: Low), whereby the voltage held in the sample capacitance 272 is output to the amplifier 263.

After that, the timing generation unit 25 turns the horizontal reset transistor 256 off (φHCLR: Low), and the input voltage Vin (for example, aV) is input.

Subsequently, while the input voltage Vin is kept constant (for example, aV), at a timing T1 when the horizontal blanking period is switched to the video signal period, the timing generation unit 25 turns the sample-and-hold switch 271 of the sample-and-hold unit 262 on (φHSH: High) and turns the switch 282 of the voltage stabilizer 247 on (φCSSW: High). In this case, at the timing T1 when the horizontal blanking period is switched to the video signal period, current $I_{Vref}$ that flows from the reference voltage generation unit 246 is reduced by $\Delta I_{amp}$. Therefore, at the timing T1 when the horizontal blanking period is switched to the video signal period, the timing generation unit 25 turns the switch 282 of the voltage stabilizer 247 on (φCSSW: High), thereby causing the current $I_{cs}$ to flow and causing the current $I_{cs}$ to have the same current value as $\Delta I_{amp}$. Consequently, the current $I_{Vref}$ that flows from the reference voltage generation unit 246 is kept constant ($I_{Vref}=I_{amp}+I_{cs}$).

As a result, the current $I_{SF}$ that flows into the source follower transistor 281 of the reference voltage generation unit 246 is kept constant ($I_{SF}=I_{Vref}+I_{load}$). Therefore, the reference voltage Vref output by the reference voltage generation unit 246 always becomes a constant voltage in accordance with the Formula (1). Thus, since the reference voltage Vref output by the reference voltage generation unit 246 can be kept constant whether the horizontal blanking period or the video signal period, it is possible to reliably prevent a signal output level during the video signal period from increasing with respect to the constant voltage during the horizontal blanking period.

According to the first embodiment, the timing generation unit 25 controls the reference voltage Vref input to the amplifier 263. Therefore, it is possible to achieve a small-sized chip and to reduce power consumption.

According to the first embodiment, only the voltage stabilizer 247 is provided to be connected between the amplifier 263 and the reference voltage generation unit 246 on one end side, connected to the ground on the other end side, and configured to stabilize the reference voltage Vref output by the reference voltage generation unit 246. The reference voltage Vref output by the reference voltage generation unit 246 is thus kept constant whether the horizontal blanking period or the video signal period, whereby it is possible to reliably prevent the signal output level during the video signal period from increasing with respect to the constant voltage during the horizontal blanking period. Therefore, it is possible to achieve a small-sized chip and to reduce the power consumption.

Second Embodiment

Next, a second embodiment of the present invention will be described. An endoscope system according to the second embodiment has a configuration similar to that of the first embodiment, but has a different circuit configuration of a first chip. More specifically, although the voltage stabilizer 247 according to the first embodiment is provided between the reference voltage generation unit 246 and the ground GND, a voltage stabilizer according to the second embodiment is provided between the power supply voltage VDD and the reference voltage generation unit 246. Furthermore, the voltage stabilizer according to the second embodiment has a different drive timing. Hereinafter, therefore, the circuit configuration of the first chip according to the second embodiment will be described, and operation of the first chip will then be described. Elements similar to those of the endoscope system 1 according to the first embodiment are provided with the same reference signs, and descriptions thereof are omitted.

Configuration of First Chip

Figure 6:
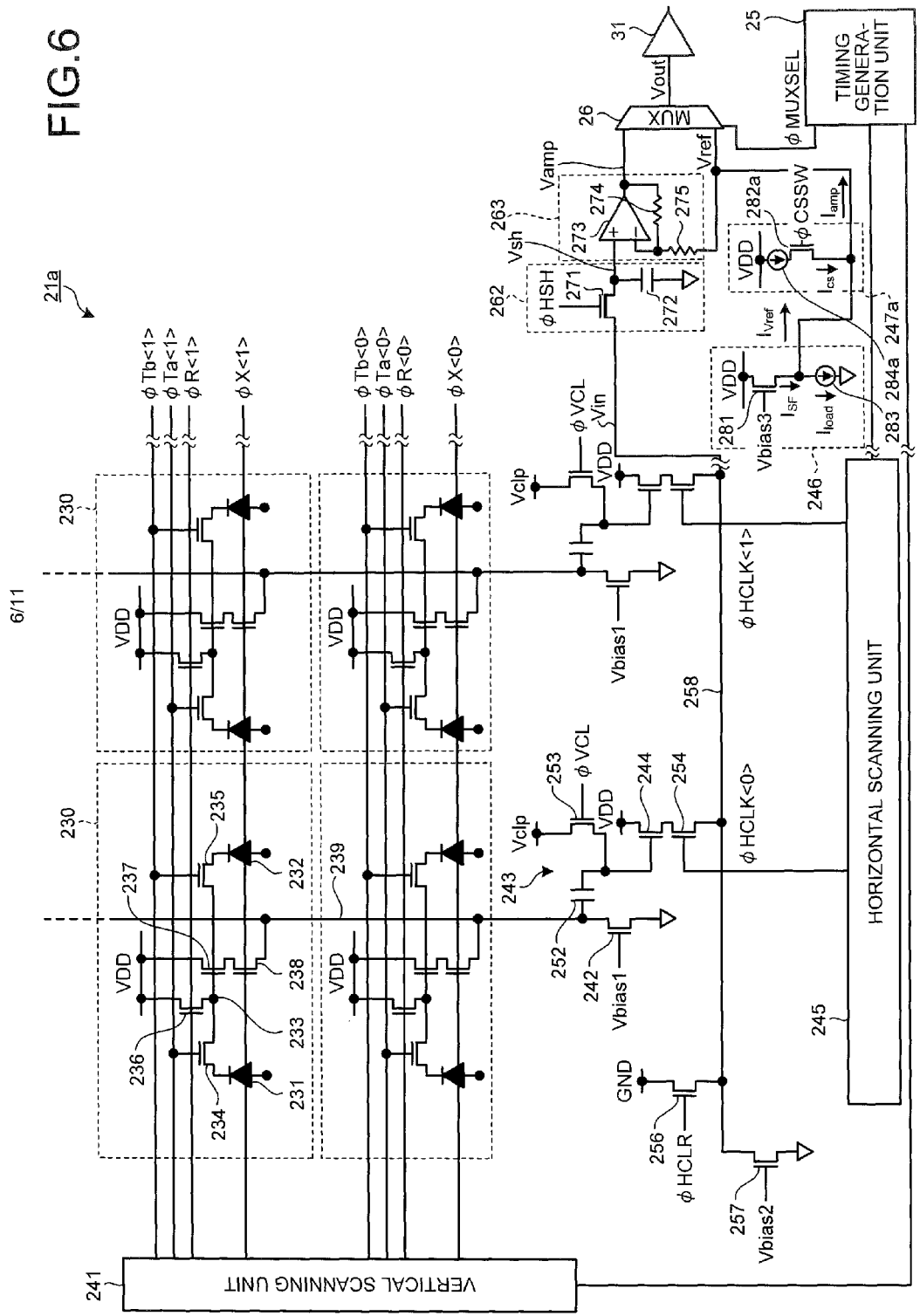
FIG. 6 is a circuit diagram illustrating a configuration of a first chip according to a second embodiment of the present invention.

FIG. 6 is a circuit diagram illustrating the configuration of the first chip according to the second embodiment. A first chip 21a illustrated in FIG. 6 has a voltage stabilizer 247a in place of the voltage stabilizer 247 according to the first embodiment.

The voltage stabilizer 247a is provided between the power supply voltage VDD and the reference voltage generation unit 246 and keeps the reference voltage generated by the reference voltage generation unit 246 during the horizontal blanking period and the video signal period, constant (stabilization). The voltage stabilizer 247a has a switch 282a (transistor). The switch 282a is connected, on one end side, to one end side of a constant current source 284a and connected to the reference voltage generation unit 246 on the other end side. A signal line is connected to a gate of the switch 282a, and the drive signal ϕCSSW is supplied from the timing generation unit 25 to the signal line. The voltage stabilizer 247a is turned off when the drive signal ϕCSSW is input from the timing generation unit 25 to the gate of the switch 282a during the horizontal blanking period of the imaging unit 20, whereby the current $I_{cs}$ stops. Consequently, the reference voltage Vref input to the operational amplifier 273 of the amplifier 263 is kept constant whether the horizontal blanking period or the video signal period.

Operation of First Chip

Figure 7:
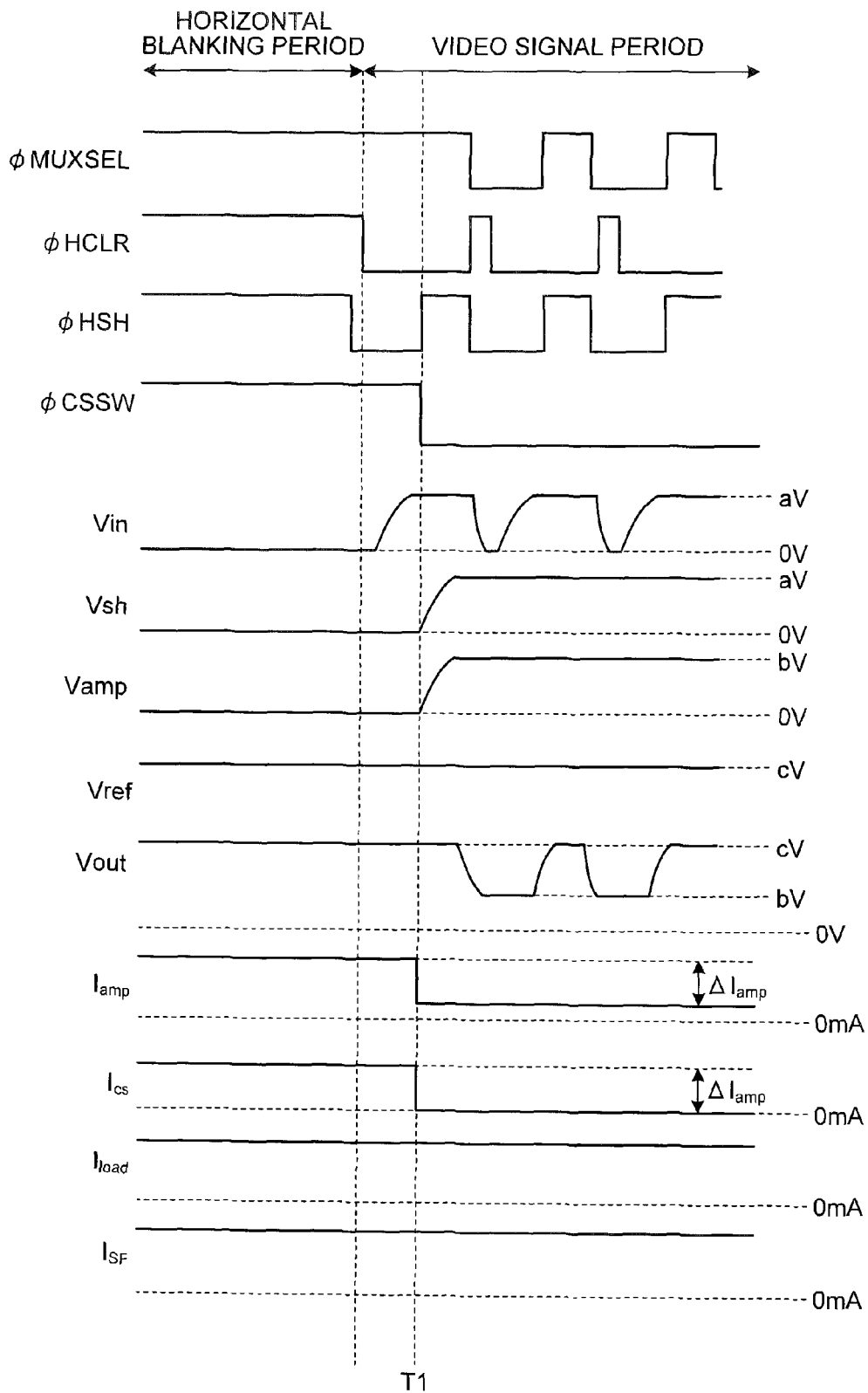
FIG. 7 is a timing chart illustrating a drive timing of the first chip according to the second embodiment of the present invention.

Next, the operation of the first chip 21a will be described. FIG. 7 is a timing chart illustrating a drive timing of the first chip 21a. In FIG. 7, in order from the highest stage, the drive signals ϕMUXSEL, ϕHCLR, ϕHSH, ϕCSSW, the input voltage Vin, the voltage Vsh, the voltage Vamp, the reference voltage Vref, the output voltage Vout, the current $I_{amp}$, the current $I_{cs}$, the current $I_{load}$, and the current $I_{SF}$ are illustrated. In FIG. 7, a description of the operation similar to that of the first embodiment is omitted, and only the drive timing until the first chip 21a is switched from the horizontal blanking period to the video signal period will be described.

As illustrated in FIG. 7, during the horizontal blanking period, the timing generation unit 25 turns the switch 282a of the voltage stabilizer 247a on (ϕCSSW: High) during the horizontal blanking period of the first chip 21a. In this case, the current $I_{amp}$ that flows into the amplifier 263 is the sum of the current $I_{Vref}$ output from the reference voltage generation unit 246 and the current $I_{cs}$ output from the voltage stabilizer 247a ($I_{amp}=I_{Vref}+I_{cs}$).

After that, the timing generation unit 25 turns the switch 282a of the voltage stabilizer 247a off (ϕCSSW: Low) at the timing T1 when the first chip 21a is switched from the horizontal blanking period to the video signal period. In this case, the current $I_{cs}$ output from the voltage stabilizer 247a stops. At this time, the current $I_{cs}$ is caused to have the same current value as $\Delta I_{amp}$, whereby a change of the current $I_{amp}$ is cancelled, and the current $I_{Vref}$ is always kept constant.

As a result, with regard to the current $I_{SF}$ that flows into the source follower transistor 281 of the reference voltage generation unit 246, the value of the sum of the current $I_{Vref}$ and the current $I_{load}$ ($I_{SF}=I_{Vref}+I_{load}$) is kept constant, and the reference voltage Vref output by the reference voltage generation unit 246 always becomes a constant voltage. Thus, since the reference voltage Vref output by the reference voltage generation unit 246 can be kept constant whether the horizontal blanking period or the video signal period, it is possible to reliably prevent the signal output level during the video signal period from increasing with respect to the constant voltage during the horizontal blanking period.

According to the second embodiment, only the voltage stabilizer 247a is provided to be connected between the amplifier 263 and the reference voltage generation unit 246 on one end side, connected to the power supply voltage VDD on the other end side, and configured to stabilize the reference voltage Vref output by the reference voltage generation unit 246. The reference voltage Vref output by the reference voltage generation unit 246 is thus kept constant whether the horizontal blanking period or the video signal period, whereby it is possible to reliably prevent the signal output level during the video signal period from increasing with respect to the constant voltage during the horizontal blanking period. Therefore, it is possible to achieve a small-sized chip and to reduce the power consumption.

Third Embodiment

Next, a third embodiment of the present invention will be described. An endoscope system according to the third embodiment has a configuration similar to that of the first embodiment, but has a different circuit configuration of a first chip. More specifically, a reset level of the horizontal reset transistor 256 according to the first embodiment is set higher than the voltage during the video signal period. In the third embodiment, a voltage stabilizer that generates a reference voltage Vref' different from the reference voltage Vref is provided on one end side of the horizontal reset transistor 256, and the voltage stabilizer that generates the reference voltage Vref' is further provided in a configuration of a reset unit. Hereinafter, therefore, the circuit configuration of the first chip according to the third embodiment will be described, and operation of the first chip will then be described. Elements similar to those of the endoscope system 1 according to the first embodiment are provided with the same reference signs, and descriptions thereof are omitted.

Configuration of First Chip

Figure 8:
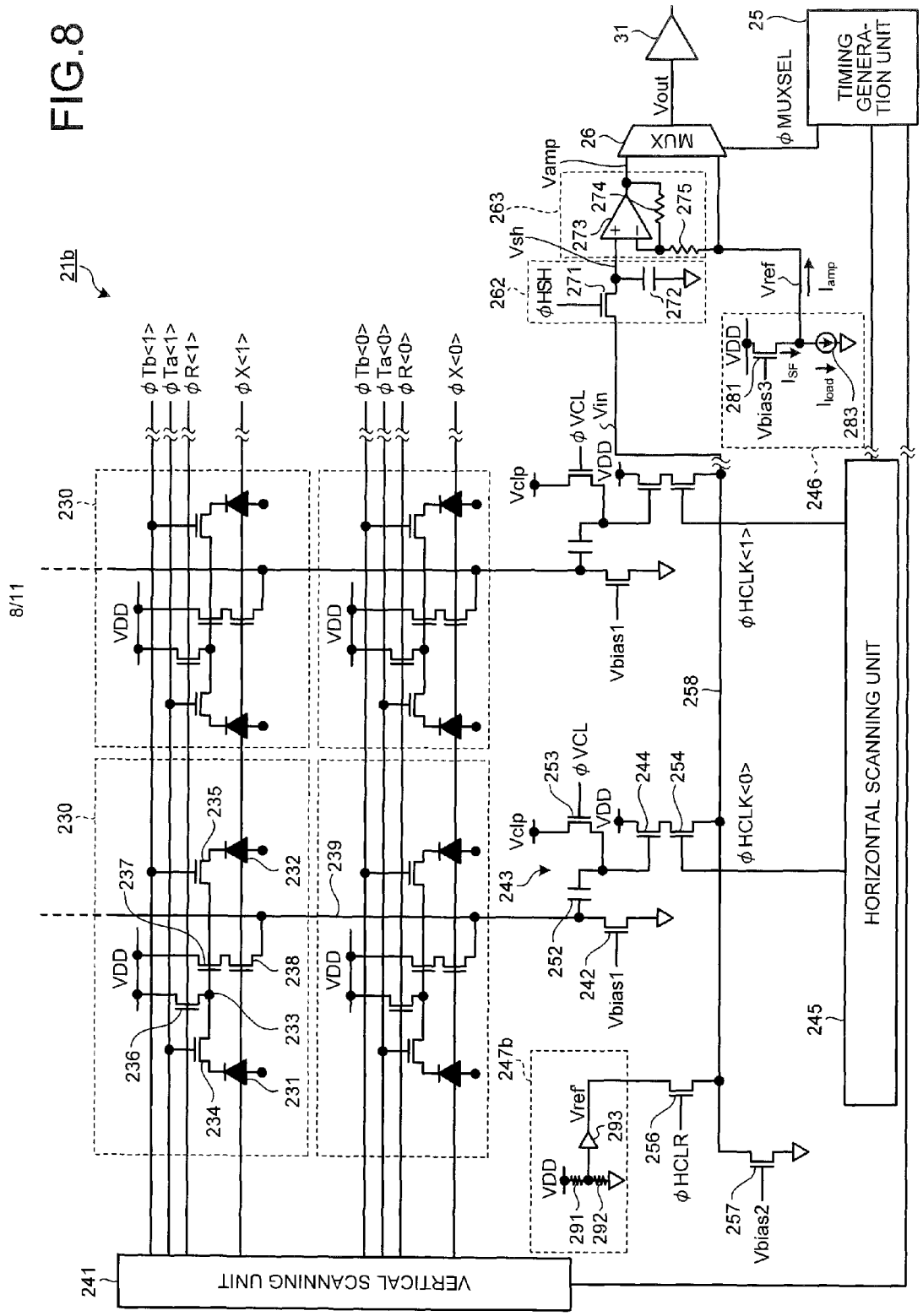
FIG. 8 is a circuit diagram illustrating a configuration of a first chip according to a third embodiment of the present invention.

FIG. 8 is a circuit diagram illustrating the configuration of the first chip according to the third embodiment. A first chip 21b illustrated in FIG. 8 has a voltage stabilizer 247b in place of the voltage stabilizer 247 according to the first embodiment.

The voltage stabilizer 247b is coupled to the horizontal transfer line 258 via the horizontal reset transistor 256 and stabilizes the reference voltage generated by the reference voltage generation unit 246 during the horizontal blanking period. The voltage stabilizer 247b has a resistance voltage dividing circuit and a buffer 293. The resistance voltage dividing circuit includes two resistors 291 and 292. The resistance voltage dividing circuit including the two resistors 291 and 292 is connected to the power supply voltage VDD on one end side and connected to the ground GND on the other end side. A branch point of the resistance voltage dividing circuit is connected to an input end of the buffer 293. An output end of the buffer 293 is connected to one end side of the horizontal reset transistor 256. The reference voltage Vref' output by the voltage stabilizer 247b is set to a voltage higher than the voltage (Vsh) during the video signal period (Vref'>Vsh). In other words, the voltage stabilizer 247b sets the reset level of the horizontal reset transistor 256 higher than the voltage during the video signal period (Vref'>Vsh).

Operation of First Chip

Figure 9:
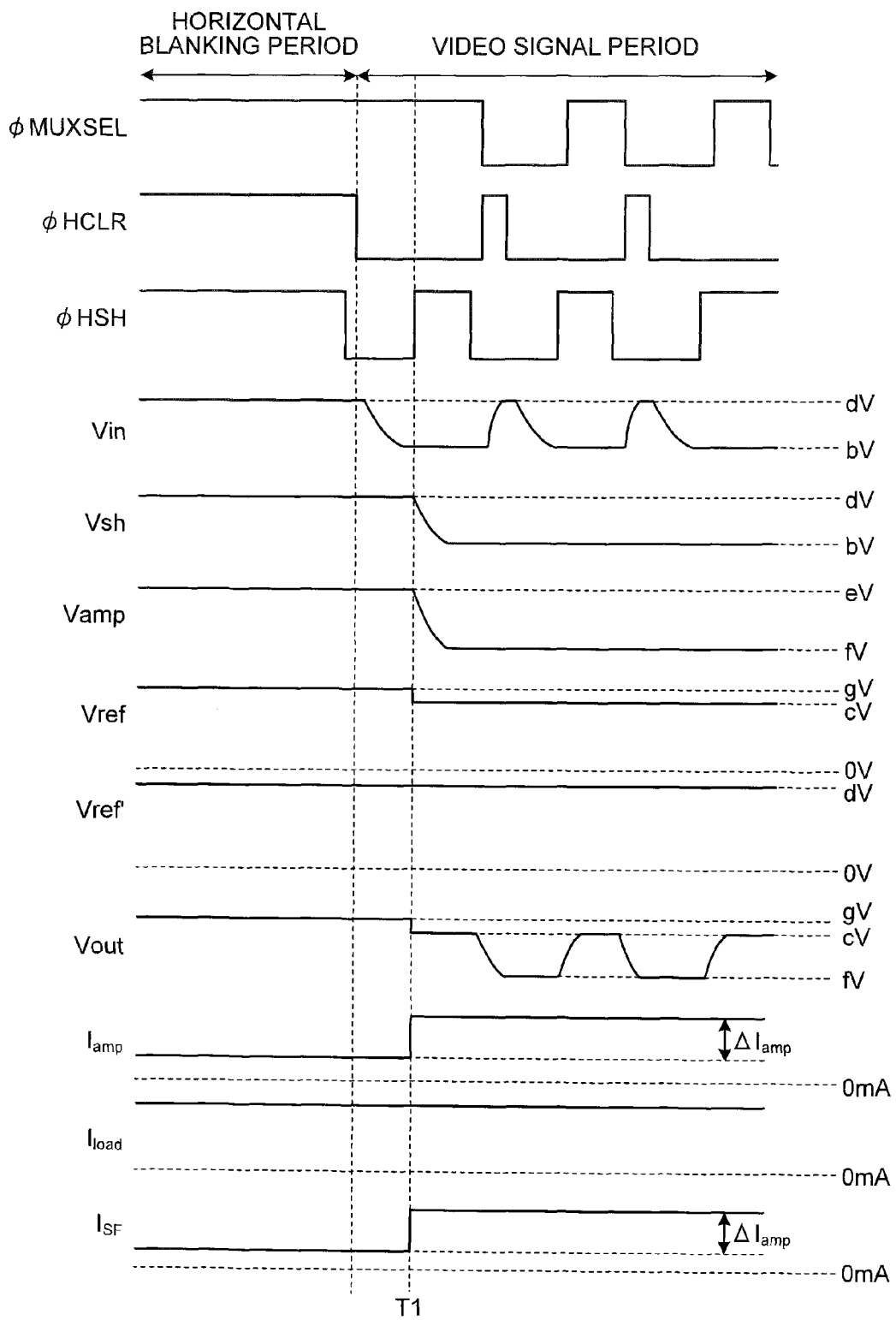
FIG. 9 is a timing chart illustrating a drive timing of the first chip according to the third embodiment of the present invention.

Next, the operation of the first chip 21b will be described. FIG. 9 is a timing chart illustrating a drive timing of the first chip 21b. In FIG. 9, in order from the highest stage, the drive signals φMUXSEL, φHCLR, φHSH, the input voltage Vin, the voltage Vsh, the voltage Vamp, the reference voltage Vref, the reference voltage Vref', the output voltage Vout, the current $I_{amp}$, the current $I_{load}$, and the current $I_{SF}$ are illustrated. In FIG. 9, the drive timing from input of the imaging signal as the input voltage Vin from the light receiving unit 23 until output of the imaging signal will be described.

First, as illustrated in FIG. 9, during the horizontal blanking period of the imaging unit 20, the timing generation unit 25 turns the multiplexer 26 on (φMUXSEL: High), turns the horizontal reset transistor 256 on (φHCLR: High), and turns the sample-and-hold switch 271 of the sample-and-hold unit 262 on (φHSH: High). Consequently, the reference voltage Vref' (for example, dV) is input to the input voltage Vin and the voltage Vsh of the sample capacitance 272, and the reference voltage Vref is output from the multiplexer 26 to the output unit 31 as the output voltage Vout (for example, gV).

After that, the timing generation unit 25 turns the sample-and-hold switch 271 of the sample-and-hold unit 262 off (φHSH: Low) and turns the horizontal reset transistor 256 off (φHCLR: Low). The input voltage Vin (for example, bV) is thus input.

Subsequently, at the timing T1 when the horizontal blanking period is switched to the video signal period, the timing generation unit 25 turns the sample-and-hold switch 271 of the sample-and-hold unit 262 on (φHSH: High) and inputs the input voltage Vin (for example, bV) to the sample capacitance 272 (voltage Vsh). In this case, the current $I_{amp}$ that flows from the reference voltage generation unit 246 has a value reduced by $\Delta I_{amp}$ during the horizontal blanking period as compared with that during the video signal period. Therefore, the reference voltage Vref during the video signal period is greater than the reference voltage Vref during the horizontal blanking period (gV>cV). The current $I_{amp}$ is represented by the following Formula (3).

$$I_{amp} = \frac{1}{R1}(V_{ref} - V_{sh}) \qquad (3)$$

In this case, the voltage Vsh during the video signal period is invariably made smaller than the voltage Vsh during the horizontal blanking period (dV>bV), whereby the value during the horizontal blanking period can be reduced as compared with that during the video signal period. A condition is set such that a fluctuation of the reference voltage Vref with respect to a fluctuation of the current $I_{amp}$ is sufficiently smaller than a fluctuation amount of the voltage Vsh.

According to the third embodiment, the voltage stabilizer 247b is provided at the horizontal transfer line 258 to generate and output the reference voltage Vref' different from the reference voltage Vref generated by the reference voltage generation unit 246. Then, the reference voltage Vref' is set as the reset level of the horizontal transfer line 258, the current $I_{amp}$ that flows from the reference voltage generation unit 246 during the horizontal blanking period is reduced, and the reference voltage Vref during the video signal period is invariably made greater than the reference voltage Vref during the horizontal blanking period. Consequently, it is possible to reliably prevent the signal output level during the video signal period from increasing with respect to the constant voltage during the horizontal blanking period. Therefore, it is possible to achieve a small-sized chip and to reduce the power consumption.

Fourth Embodiment

Next, a fourth embodiment of the present invention will be described. An endoscope system according to the fourth embodiment has a configuration similar to that of the first embodiment, but has a different circuit configuration of a first chip. More specifically, the first chip according to the fourth embodiment has a different configuration of a sample-and-hold unit. Hereinafter, therefore, the circuit configuration of the first chip according to the fourth embodiment will be described, and operation of the first chip will then be described. Elements similar to those of the endoscope system 1 according to the first embodiment are provided with the same reference signs, and descriptions thereof are omitted.

Configuration of First Chip

Figure 10:
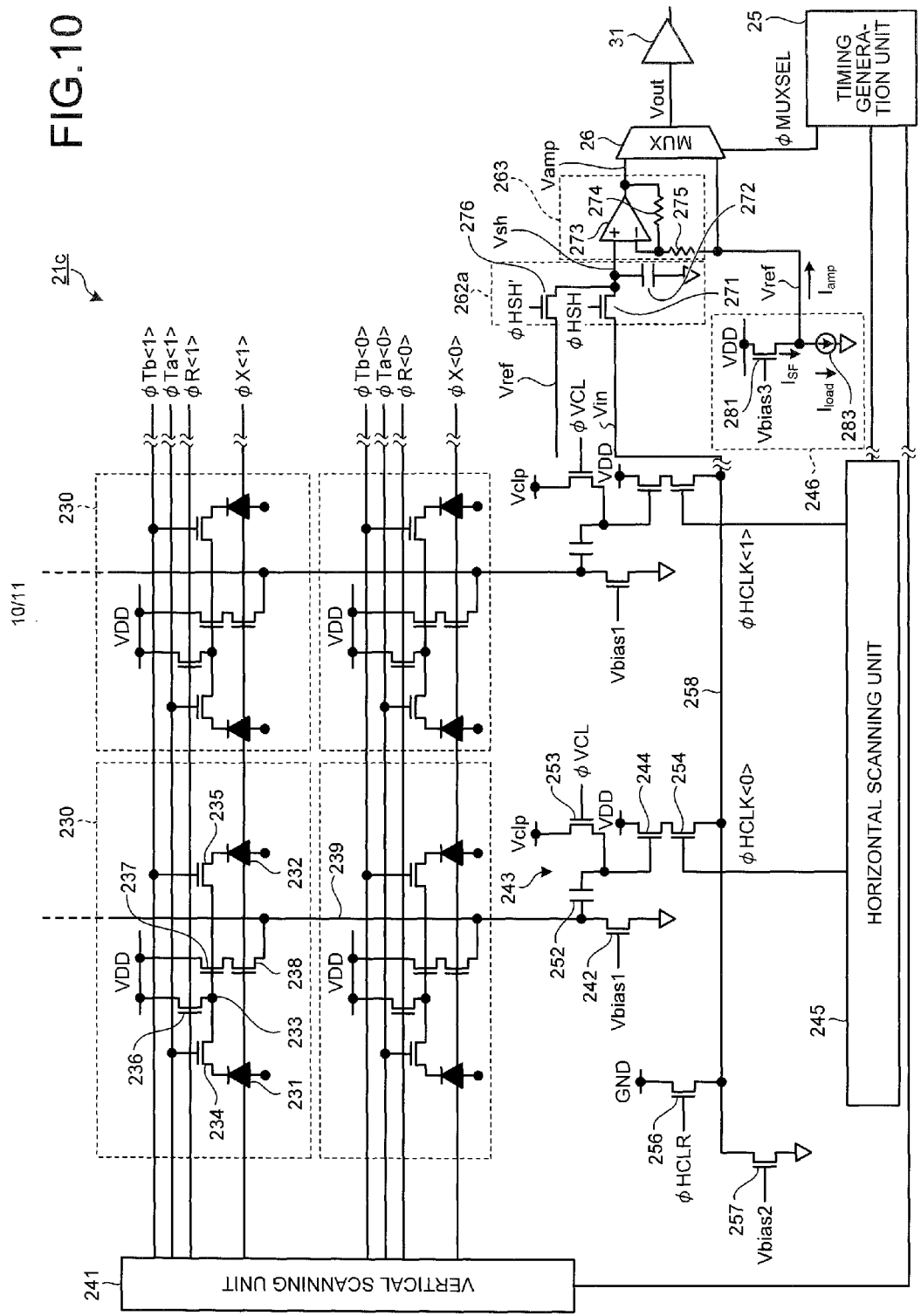
FIG. 10 is a circuit diagram illustrating a configuration of a first chip according to a fourth embodiment of the present invention.

FIG. 10 is a circuit diagram illustrating the configuration of the first chip according to the fourth embodiment. A first chip 21c illustrated in FIG. 10 has a sample-and-hold unit 262a in place of the sample-and-hold unit 262 according to the first embodiment. Furthermore, the first chip 21c illustrated in FIG. 10 is configured such that the voltage stabilizer 247 according to the first embodiment is omitted, and the reference voltage generation unit 246 is connected to the amplifier 263 and the multiplexer 26.

The sample-and-hold unit 262a has a switch 276 (transistor) in addition to the sample-and-hold unit 262 according to the first embodiment. The switch 276 is connected to a signal line on one end side and connected between the sample-and-hold switch 271 and the sample capacitance 272 on the other end side. The reference voltage Vref generated by the reference voltage generation unit 246 is supplied to the signal line. Another signal line is connected to a gate of the switch 276, and a drive signal φHSH' is supplied from the timing generation unit 25 to the signal line.

The sample-and-hold unit 262a configured in this manner is turned on when the drive signal φHSH' is input from the timing generation unit 25 to the gate of the switch 276 during the horizontal blanking period of the imaging unit 20. The sample-and-hold unit 262a then causes the sample capacitance 272 to hold the reference voltage Vref. The sample-and-hold unit 262a is turned off when the drive signal φHSH' input from the timing generation unit 25 to the gate of the sample-and-hold switch 271 stops. The sample-and-hold unit 262a then outputs the voltage (signal) held in the sample capacitance 272 to the operational amplifier 273.

Operation of First Chip

Figure 11:
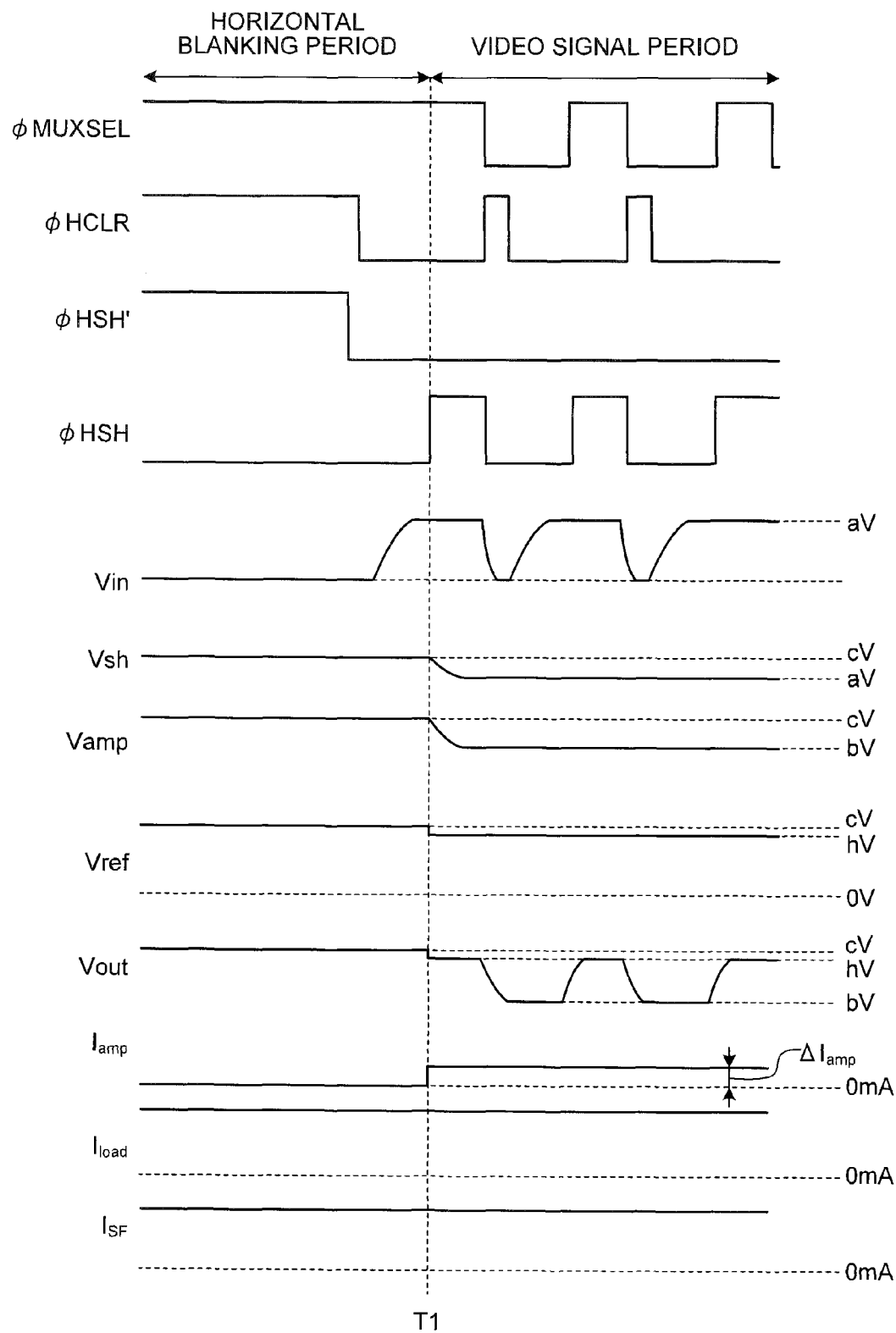
FIG. 11 is a timing chart illustrating a drive timing of the first chip according to the fourth embodiment of the present invention.

Next, the operation of the first chip 21c will be described. FIG. 11 is a timing chart illustrating a drive timing of the first chip 21c. In FIG. 11, in order from the highest stage, the drive signals φMUXSEL, φHCLR, φHSH', φHSH, the input voltage Vin, the voltage Vsh, the voltage Vamp, the reference voltage Vref, the output voltage Vout, the current $I_{amp}$, the current $I_{load}$, and the current $I_{SF}$ are illustrated.

First, as illustrated in FIG. 11, during the horizontal blanking period, the timing generation unit 25 turns the multiplexer 26 on (φMUXSEL: High), turns the horizontal reset transistor 256 on (φHCLR: High), and turns the switch 276 of the sample-and-hold unit 262a on (φHSH': High). Consequently, the reference voltage Vref (for example, cV) is input as the voltage Vsh (for example, cV) of the sample capacitance 272, and further output from the multiplexer 26 to the output unit 31 as the output voltage Vout (for example, cV).

Next, the timing generation unit 25 turns the switch 276 of the sample-and-hold unit 262a off (φHSH': Low) and turns the horizontal reset transistor 256 off (φHCLR: Low). The input voltage Vin (for example, aV) is thus input.

After that, at the timing T1 when the horizontal blanking period is switched to the video signal period, the timing generation unit 25 turns the sample-and-hold switch 271 of the sample-and-hold unit 262a on (φHSH: High), thereby inputting the input voltage Vin (for example, aV) to the sample capacitance 272 (voltage Vsh). In this case, the current $I_{amp}$ that flows from the reference voltage generation unit 246 is represented by the Formula (3). Therefore, the voltage Vsh during the horizontal blanking period is set as the reference voltage Vref, and the current $I_{amp}$ is set to zero, whereby the reference voltage Vref during the horizontal blanking period is made greater than that during any period (cV>hV). As a result, since the reference voltage Vref during the video signal period is invariably made greater than the reference voltage Vref during the horizontal blanking period, it is possible to reliably prevent the signal output level during the video signal period from increasing with respect to the constant voltage during the horizontal blanking period.

According to the fourth embodiment, the switch 276 is provided to be capable of inputting the reference voltage Vref generated by the reference voltage generation unit 246 to the sample capacitance 272 of the sample-and-hold unit 262a. Then, the reference voltage Vref during the video signal period is invariably made greater than the reference voltage Vref during the horizontal blanking period. Consequently, it is possible to reliably prevent the signal output level during the video signal period from increasing with respect to the constant voltage during the horizontal blanking period. Therefore, it is possible to achieve a small-sized chip and to reduce the power consumption.

In the fourth embodiment, the reference voltage Vref generated by the reference voltage generation unit 246 is supplied to the sample-and-hold unit 262a. Alternatively, the reference voltage Vref' generated by the voltage stabilizer 247b of the third embodiment may be supplied.

According to some embodiments, it is possible to achieve a small-sized chip and to reduce power consumption.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image sensor comprising:
a plurality of pixels arranged in a two-dimensional matrix form and configured to receive light from outside and generate and output an imaging signal depending on an amount of the received light;
a transfer unit configured to transfer the imaging signal output from each of the plurality of pixels;
a sample-and-hold unit configured to hold and output the imaging signal transferred from the transfer unit;
a reference voltage generation unit configured to generate and output a reference voltage;
an amplifier connected to the sample-and-hold unit and to the reference voltage generation unit and configured to amplify and output the imaging signal input from the sample-and-hold unit using the reference voltage as a reference; and
a control unit configured to control the reference voltage to be input to the amplifier during at least one of a horizontal blanking period and a video signal period of the imaging signal.

2. The image sensor according to claim 1, further comprising a voltage stabilizer connected between the amplifier and the reference voltage generation unit on one end of the voltage stabilizer, connected to a ground on another end of the voltage stabilizer, and configured to keep the reference voltage output by the reference voltage generation unit constant, wherein
the control unit is configured to drive the voltage stabilizer during the video signal period of the imaging signal to control the reference voltage to be input to the amplifier.

3. The image sensor according to claim 1, further comprising a voltage stabilizer connected between the amplifier and the reference voltage generation unit on one end of the voltage stabilizer, connected to a power supply voltage on another end of the voltage stabilizer, and configured to keep the reference voltage output by the reference voltage generation unit constant, wherein
the control unit is configured to drive the voltage stabilizer during the horizontal blanking period of the imaging signal to control the reference voltage to be input to the amplifier.

4. The image sensor according to claim 1, further comprising a voltage stabilizer connected to the transfer unit and configured to generate and output a different voltage from the reference voltage, wherein the control unit is configured to drive the voltage stabilizer during the horizontal blanking period of the imaging signal to input the different voltage to the sample-and-hold unit, thereby to control the reference voltage to be input to the amplifier.

5. The image sensor according to claim 1, wherein the sample-and-hold unit is connected to the reference voltage generation unit and is configured to further hold the reference voltage generated by the reference voltage generation unit, and the control unit is configured to cause the reference voltage held by the sample-and-hold unit to be output to the amplifier during the horizontal blanking period of the imaging signal, thereby to control the reference voltage to be input to the amplifier.

6. An imaging device comprising the image sensor according to claim 1.

7. An endoscope comprising an insertion portion that has the imaging device according to claim 6 on a distal end of the insertion portion.

8. An endoscope system comprising:

the endoscope according to claim 7; and a processing device configured to convert the imaging signal into an image signal.

* * * * *